United States Patent [19]

Haas et al.

[11] Patent Number: 5,294,596
[45] Date of Patent: Mar. 15, 1994

[54] HETEROCYCLYLTRIAZOLINONES AND HERBICIDAL USE

[75] Inventors: Wilhelm Haas, Pulheim; Kurt Findeisen; Karl-Heinz Linker, both of Leverkusen; Klaus Lürssen, Bergisch Gladbach; Hans-Joachim Santel, Leverkusen; Robert R. Schmidt, Bergisch Gladbach, all of Fed. Rep. of Germany

[73] Assignee: Bayer Aktiengesellschaft, Leverkusen, Fed. Rep. of Germany

[21] Appl. No.: 95,628

[22] Filed: Jul. 21, 1993

[30] Foreign Application Priority Data

Jul. 28, 1992 [DE] Fed. Rep. of Germany ....... 4224929

[51] Int. Cl.$^5$ .................. A01N 43/653; A01N 43/84; C07D 413/04; C07D 417/04
[52] U.S. Cl. ..................... 504/225; 504/253; 504/262; 504/263; 504/265; 504/273; 544/134; 546/209; 548/129; 548/130; 548/132; 548/133; 548/138; 548/141; 548/143; 548/144; 548/263.8; 548/264.2
[58] Field of Search .................. 544/134; 546/209; 548/129, 130, 132, 133, 138, 141, 143, 144, 263.8, 264.2; 504/225, 253, 262, 263, 265, 273

[56] References Cited

FOREIGN PATENT DOCUMENTS 2042660 3/1972 Fed. Rep. of Germany.

OTHER PUBLICATIONS

Nagarajan et al, *Chemical Abstracts*, vol. 117 (1993) No. 128,058b.
Dornow et al, *Chemical Abstracts*, vol. 64 (1966), 8173g.

*Primary Examiner*—Robert W. Ramsuer
*Attorney, Agent, or Firm*—Sprung Horn Kramer & Woods

[57] ABSTRACT

The invention relates to novel heterocyclyltriazolinones of the general formula (I)

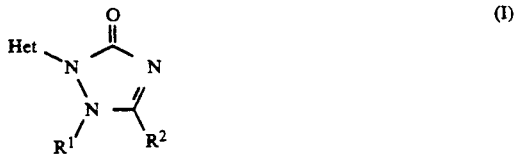

in which
R$^1$ represents hydrogen or represents alkyl or cycloalkyl, each of which is optionally substituted,
R$^2$ represents hydrogen, hydroxyl, mercapto or halogen or represents alkyl, alkenyl, alkinyl, cycloalkyl, alkoxy, alkylthio, alkylsulphinyl, alkylsulphonyl, arylalkyl, amino or heterocyclyl, each of which is optionally substituted, and
Het represents an optionally substituted heterocycle of the formula

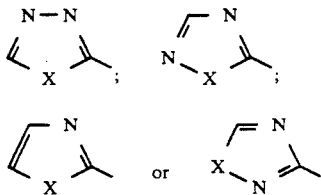

in which
X in each case represents oxygen, sulphur, an NH group or an N-alkyl group, a process for their preparation and their use as herbicides.

15 Claims, No Drawings

HETEROCYCLYLTRIAZOLINONES AND HERBICIDAL USE

The invention relates to novel heterocyclyltriazolinones, a process for their preparation and their use as herbicides.

It is known that certain aminocarbonyltriazolinones such as, for example, the compound 1-{1-[1-(2,4-dichlorophenyl)-1-cyano]-ethyl-aminocarbonyl]}-3-dimethylamino-4-methyl-1,2,4-triazolin-5-one or the compound 1-{1-[1-(4-chlorophenyl)-1-cyano]-propyl-aminocarbonyl]}-3-dimethylamino-4-methyl-1,2,4-triazolin-5-one have herbicidal properties (cf., for example, EP 283,876).

The herbicidal activity of these previously known compounds against problem weeds, like their tolerability for important crop plants, however, is not completely satisfactory in all areas of application.

New heterocyclyltriazolinones of the general formula (I)

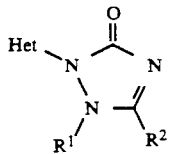

in which
R$^1$ represents hydrogen, or represents alkyl or cycloalkyl, each of which is optionally substituted,
R$^2$ represents hydrogen, hydroxyl, mercapto or halogen or represents alkyl, alkenyl, alkinyl, cycloalkyl, alkoxy, alkylthio, alkylsulphinyl, alkylsulphonyl, arylalkyl, amino or heterocyclyl, each of which is optionally substituted, and
Het represents an optionally substituted heterocycle of the formula

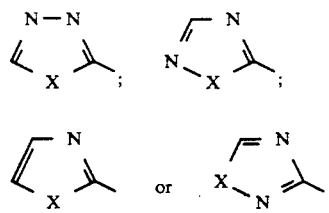

in which
X in each case represents oxygen, sulphur, an NH group or an N-alkyl group,
have now been found.

Depending on the nature of the substituents, the compounds of the formula (I) can optionally exist as geometric and/or optical isomers or isomer mixtures of variable composition. Both the pure isomers and the isomer mixtures are claimed according to the invention.

It has furthermore been found that the new heterocyclyltriazolinones of the general formula (I)

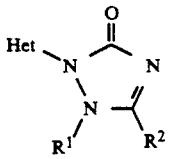

in which
R$^1$ represents hydrogen, or represents alkyl or cycloalkyl, each of which is optionally substituted,
R$^2$ represents hydrogen, hydroxyl, mercapto, halogen or represents alkyl, alkenyl, alkinyl, cycloalkyl, alkoxy, alkylthio, alkylsulphinyl, alkylsulphonyl, amino or heterocyclyl, each of which is optionally substituted, and
Het represents an optionally substituted heterocycle of the formula

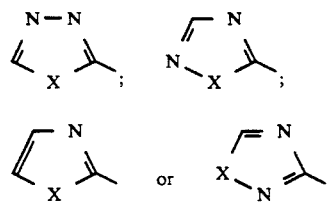

in which
X in each case represents oxygen, sulphur, an NH group or an N-alkyl group,
are obtained when heterocycles of the formula (II), Het-E (II)

in which
Het has the abovementioned meaning and
E represents an electron-attracting leaving group,
are reacted with triazolinones of the formula (III)

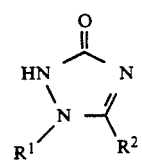

in which
R$^1$ and R$^2$ have the abovementioned meaning,
if appropriate in the presence of a diluent and if appropriate in the presence of a reaction auxiliary.

Finally, it has been found that the new heterocyclyltriazolinones of the general formula (I) have herbicidal properties.

Surprisingly, the heterocyclyltriazolinones of the general formula (I) according to the invention have a significantly better herbicidal activity against problem weeds and at the same time a comparatively good tolerability for important crop plants in comparison to the aminocarbonyltriazolinones known from the prior art, such as, for example, the compound 1-{1-[1-(2,4-dichlorophenyl)-1-cyano]-ethyl-aminocarbonyl]}-3-dimethylamino-4-methyl-1,2,4-triazolin-5-one or the compound 1-{1-[1-(4-chlorophenyl)-1-cyano]-propyl-aminocarbonyl]}-3-dimethylamino-4-methyl-1,2,4-triazolin-5-one, which are closely related compounds chemically and with respect to their action.

Formula (I) provides a general definition of the heterocyclyltriazolinones according to the invention. Preferred compounds of the formula (I) are those in which $R^1$ represents hydrogen, or straight-chain or branched alkyl having 1 to 6 carbon atoms, which is optionally monosubstituted or polysubstituted by identical or different substituents, suitable alkyl substituents being:
halogen, or alkoxy, alkylthio, alkylamino or dialkylamino each having 1 to 4 carbon atoms in the individual alkyl moieties and each of which is straight-chain or branched, and
additionally represents cycloalkyl having 3 to 8 carbon atoms;

$R^2$ represents hydrogen, hydroxyl, mercapto, amino, halogen or straight-chain or branched alkyl having 1 to 6 carbon atoms, which is optionally monosubstituted or polysubstituted by identical or different substituents, suitable alkyl substituents being:
halogen, cyano, or alkoxy, alkylthio, alkylamino or dialkylamino each having 1 to 4 carbon atoms in the individual alkyl moieties and each of which is straight-chain or branched,
additionally represents alkenyl or alkinyl each having 2 to 6 carbon atoms and each of which is straight-chain or branched, alkoxy, alkylthio, alkylsulphinyl or alkylsulphonyl each having 1 to 6 carbon atoms and each of which is straight-chain or branched, or cycloalkyl having 3 to 8 carbon atoms;
additionally represents arylalkyl having 6 to 10 carbon atoms in the aryl moiety and 1 to 6 carbon atoms in the straight-chain or branched alkyl moiety which is optionally monosubstituted or polysubstituted in the aryl moiety by identical or different substituents, suitable aryl substituents being:
halogen, cyano, nitro, or alkyl, alkoxy or alkylthio each having 1 to 4 carbon atoms and each of which is straight-chain or branched, halogenoalkyl, halogenoalkoxy or halogenoalkylthio each having 1 to 4 carbon atoms and 1 to 9 identical or different halogen atoms and each of which is straight-chain or branched, alkoxycarbonyl or alkoximinoalkyl each having 1 to 4 carbon atoms in the individual alkyl moieties and each of which is straight-chain or branched, and phenyl which is optionally monosubstituted or polysubstituted by identical or different halogen substituents and/or straight-chain or branched alkyl substituents having 1 to 4 carbon atoms;
and additionally represents a radical

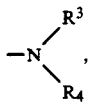

Het represents a heterocycle of the formula

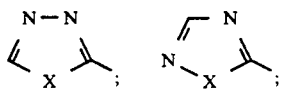

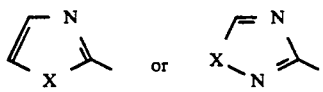

which is optionally monosubstituted or polysubstituted by identical or different substituents, suitable substituents in each case being:
halogen, hydroxyl, mercapto, amino, cyano, nitro or carbamoyl, or alkyl, alkoxy, alkylthio, alkylsulphinyl, alkylsulphonyl, alkylamino, dialkylamino, alkanoylamino; halogenoalkylcarbonylamino or alkylaminocarbonylamino each having 1 to 8 carbon atoms in the individual alkyl moieties and optionally 1 to 13 identical or different halogen atoms and each of which is straight-chain or branched, alkenyl or alkinyl each having 2 to 6 carbon atoms and each of which is straight-chain or branched, straight-chain or branched alkylideneamino having 1 to 6 carbon atoms, halogenoalkyl, halogenoalkoxy, halogenoalkylthio, halogenoalkylsulphinyl or halogenoalkylsulphonyl each having 1 to 6 carbon atoms and 1 to 13 identical or different halogen atoms and each of which is straight-chain or branched, straight-chain or branched alkoxycarbonyl having 1 to 7 carbon atoms, cycloalkyl having 3 to 8 carbon atoms and aryl, arylalkyl, arylalkylideneamino or arylalkylaminocarbonylamino each having 6 to 10 carbon atoms in the aryl moiety and optionally 1 to 4 carbon atoms in the straight-chain or branched alkyl moiety and each of which is optionally monosubstituted or polysubstituted in the aryl moiety by identical or different halogen substituents and/or straight-chain or branched alkyl and/or alkoxy substituents each having 1 to 4 carbon atoms and/or halogenoalkyl substituents having 1 to 4 carbon atoms and 1 to 9 identical or different halogen atoms, and X in each case represents oxygen, sulphur, an NH group or a straight-chain or branched N-alkyl group having 1 to 8 carbon atoms, $R^3$ represents hydrogen or straight-chain or branched alkyl having 1 to 6 carbon atoms, which is optionally monosubstituted or polysubstituted by identical or different substituents, suitable alkyl substituents being:
halogen, cyano, or alkoxy, alkylthio, alkylamino or dialkylamino each having 1 to 4 carbon atoms in the individual alkyl moieties and each of which is straight-chain or branched, and phenyl which is optionally monosubstituted or polysubstituted by identical or different halogen substituents and/or straight-chain or branched alkyl substituents having 1 to 4 carbon atoms;
additionally represents alkenyl or alkinyl each having 2 to 6 carbon atoms and each of which is straight-chain or branched, straight-chain or branched alkoxy having 1 to 6 carbon atoms or cycloalkyl having 3 to 8 carbon atoms and $R^4$ represents straight-chain or branched alkyl having 1 to 6 carbon atoms, which is optionally monosubstituted or polysubstituted by identical or different substituents, suitable alkyl substituents being:
halogen, cyano, or alkoxy, alkylthio, alkylamino or dialkylamino each having 1 to 4 carbon atoms in the individual alkyl moieties and each of which is straight-chain or branched, and phenyl which is optionally monosubstituted or polysubstituted by identical or different halogen substituents and/or straight-chain or branched alkyl substituents having 1 to 4 carbon atoms;

additionally represents alkenyl or alkinyl each having 2 to 6 carbon atoms and each of which is straight-chain or branched, straight-chain or branched alkoxy having 1 to 6 carbon atoms or cycloalkyl having 3 to 8 carbon atoms or $R^3$ and $R^4$, together with the nitrogen atom to which they are bonded, represent a saturated or unsaturated heterocycle which can optionally contain 1 to 3 further heteroatoms—in particular nitrogen, oxygen and/or sulphur, and which is optionally monosubstituted or polysubstituted by identical or different substituents, suitable heterocyclyl substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino or alkanoylamino; halogenoalkylcarbonylamino or alkylaminocarbonylamino each having 1 to 8 carbon atoms in the individual alkyl moieties and optionally 1 to 13 identical or different halogen atoms and each of which is straight-chain or branched, alkenyl or alkinyl each having 2 to 6 carbon atoms and each of which is straight-chain or branched, straight-chain or branched alkylideneamino having 1 to 6 carbon atoms, halogenoalkyl, halogenoalkoxy, halogenoalkylthio, halogenoalkylsulphinyl or halogenoalkylsulphonyl each having 1 to 6 carbon atoms and 1 to 13 identical or different halogen atoms and each of which is straight-chain or branched, straight-chain or branched alkoxycarbonyl having 1 to 7 carbon atoms, cycloalkyl having 3 to 8 carbon atoms and aryl, arylalkyl, arylalkylideneamino or arylalkylaminocarbonylamino each having 6 to 10 carbon atoms in the aryl moiety and optionally 1 to 4 carbon atoms in the straight-chain or branched alkyl moiety and each of which is optionally monosubstituted or polysubstituted in the aryl moiety by identical or different halogen substituents and/or straight-chain or branched alkyl and/or alkoxy substituents each having 1 to 4 carbon atoms and/or halogenoalkyl substituents having 1 to 4 carbon atoms and 1 to 9 identical or different halogen atoms.

Particularly preferred compounds of the formula (I) are those in which $R^1$ represents hydrogen, or straight-chain or branched alkyl having 1 to 4 carbon atoms, which is optionally monosubstituted to disubstituted by identical or different substituents, suitable alkyl substituents being:

alkoxy, alkylthio, alkylamino or dialkylamino each having 1 to 3 carbon atoms in the individual alkyl moieties and each of which is straight-chain or branched;

additionally represents straight-chain or branched halogenoalkyl having 1 to 4 carbon atoms and 1 to 9 identical or different halogen atoms—in particular fluorine, chlorine and/or bromine, additionally represents cycloalkyl having 3 to 7 carbon atoms;

$R^2$ represents hydrogen, hydroxyl, mercapto, amino, halogen or straight-chain or branched alkyl having 1 to 4 carbon atoms, which is optionally monosubstituted or disubstituted by identical or different substituents, suitable alkyl substituents being:

cyano, or alkoxy, alkylthio, alkylamino or dialkylamino each having 1 to 3 carbon atoms in the individual alkyl moieties and each of which is straight-chain or branched, additionally represents straight-chain or branched halogenoalkyl having 1 to 4 carbon atoms and 1 to 9 identical or different halogen atoms—in particular fluorine, chlorine and/or bromine, additionally represents alkenyl or alkinyl each having 2 to 5 carbon atoms and each of which is straight-chain or branched, alkoxy, alkylthio, alkylsulphinyl or alkylsulphonyl each having 1 to 4 carbon atoms and each of which is straight-chain or branched, or cycloalkyl having 3 to 7 carbon atoms;

additionally represents arylalkyl having 6 or 10 carbon atoms in the aryl moiety and 1 to 4 carbon atoms in the straight-chain or branched alkyl moiety, which is optionally monosubstituted to trisubstituted in the aryl moiety by identical or different substituents, suitable aryl substituents being:

halogen, cyano, nitro, or alkyl, alkoxy or alkylthio each having 1 to 3 carbon atoms and each of which is straight-chain or branched, halogenoalkyl, halogenoalkoxy or halogenoalkylthio each having 1 to 3 carbon atoms and 1 to 7 identical or different halogen atoms and each of which is straight-chain or branched, alkoxycarbonyl or alkoximinoalkyl each having 1 to 3 carbon atoms in the individual alkyl moieties and each of which is straight-chain or branched, and phenyl which is optionally monosubstituted to trisubstituted by identical or different halogen substituents and/or straight-chain or branched alkyl substituents having 1 to 3 carbon atoms;

and additionally represents a radical

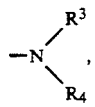

Het represents a heterocycle of the formula

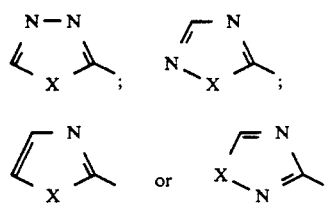

which is optionally monosubstituted to disubstituted by identical or different substituents, suitable substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino, alkanoylamino, halogenoalkylcarbonylamino or alkylaminocarbonylamino each having 1 to 6 carbon atoms in the individual alkyl moieties and optionally 1 to 13 identical or different halogen atoms—in particular fluorine, chlorine and/or bromine, and each of which is straight-chain or branched, alkenyl or alkinyl each having 2 to 5 carbon atoms and each of which is straight-chain or branched, straight-chain or branched alkylideneamino having 1 to 4 carbon atoms, halogenoalkyl, halogenoalkoxy, halogenoalkylthio, halogenoalkylsulphinyl or halogenoalkylsulphonyl each having 1 to 4 carbon atoms and 1 to 9 identical or different halogen atoms and each of which is straight-chain or branched, straight-chain or branched alkoxycarbonyl having 1 to 5 carbon atoms, cycloalkyl having 3 to 7 carbon atoms and aryl, arylalkyl, arylalkylideneamino or arylalkylaminocarbonylamino each having 6 or 10 carbon atoms in the aryl moiety and optionally 1 to 3 carbon atoms in the straight-chain or branched alkyl moiety and each of which is optionally monosubstituted to trisubstituted in the aryl moiety by identical or different halogen substituents and/or straight-chain or branched alkyl and/or alkoxy substituents each having 1 to 3 carbon atoms and/or halogenoalkyl substituents having 1 to 3 carbon atoms and 1 to 7 identical or different halogen atoms and X in each case represents oxygen, sulphur, an NH group or a straight-chain or branched N-alkyl group having 1 to 6 carbon atoms, $R^3$ represents hydrogen or straight-chain or branched alkyl having 1 to 4 carbon atoms, which is optionally monosubstituted to disubstituted by identical or different substituents, suitable alkyl substituents being:

cyano, or alkoxy, alkylthio, alkylamino or dialkylamino each having 1 to 3 carbon atoms in the individual alkyl moieties and each of which is straight-chain or branched, and phenyl which is optionally monosubstituted to trisubstituted by identical or different halogen substituents and/or straight-chain or branched alkyl substituents having 1 to 3 carbon atoms;

additionally represents straight-chain or branched halogenoalkyl having 1 to 4 carbon atoms and 1 to 9 identical or different halogen atoms—in particular fluorine, chlorine and/or bromine, additionally represents alkenyl or alkinyl each having 2 to 5 carbon atoms and each of which is straight-chain or branched, straight-chain or branched alkoxy having 1 to 4 carbon atoms or cycloalkyl having 3 to 7 carbon atoms and $R^4$ represents straight-chain or branched alkyl having 1 to 4 carbon atoms, which is optionally monosubstituted or disubstituted by identical or different substituents, suitable alkyl substituents being:

cyano, or alkoxy, alkylthio, alkylamino or dialkylamino each having 1 to 3 carbon atoms in the individual alkyl moieties and each of which is straight-chain or branched, and phenyl which is optionally monosubstituted to trisubstituted by identical or different halogen substituents and/or straight-chain or branched alkyl substituents having 1 to 3 carbon atoms;

additionally represents straight-chain or branched halogenoalkyl having 1 to 4 carbon atoms and 1 to 9 identical or different halogen atoms—in particular fluorine, chlorine and/or bromine, additionally represents alkenyl or alkinyl each having 2 to 5 carbon atoms and each of which is straight-chain or branched, straight-chain or branched alkoxy having 1 to 4 carbon atoms or cycloalkyl having 3 to 7 carbon atoms or $R^3$ and $R^4$, together with the nitrogen atom to which they are bonded, represent a saturated five- to seven-membered, monocyclic heterocycle which is optionally monosubstituted or disubstituted by identical or different substituents and which can optionally contain 1 or 2 further heteroatoms—in particular nitrogen, oxygen and/or sulphur, suitable heterocyclyl substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino, alkanoylamino, halogenoalkylcarbonylamino or alkylaminocarbonylamino each having 1 to 6 carbon atoms in the individual alkyl moieties and optionally 1 to 13 identical or different halogen atoms—in particular fluorine, chlorine and/or bromine, and each of which is straight-chain or branched, alkenyl or alkinyl each having 2 to 5 carbon atoms and each of which is straight-chain or branched, straight-chain or branched alkylideneamino having 1 to 1 carbon atoms, halogenoalkyl, halogenoalkoxy, halogenoalkylthio, halogenoalkylsulphinyl or halogenoalkylsulphonyl each having 1 to 4 carbon atoms and 1 to 9 identical or different halogen atoms and each of which is straight-chain or branched, straight-chain or branched alkoxycarbonyl having 1 to 5 carbon atoms, cycloalkyl having 3 to 7 carbon atoms and aryl, arylalkyl, arylalkylideneamino or arylalkylaminocarbonylamino each having 6 or 10 carbon atoms in the aryl moiety and optionally 1 to 3 carbon atoms in the straight-chain or branched alkyl moiety and each of which is optionally monosubstituted to trisubstituted in the aryl moiety by identical or different halogen substituents and/or straight-chain or branched alkyl and/or alkoxy substituents each having 1 to 3 carbon atoms and/or halogenoalkyl substituents having 1 to 3 carbon atoms and 1 to 7 identical or different halogen atoms.

Very particularly preferred compounds of the formula (I) are those in which $R^1$ represents hydrogen, or straight-chain or branched alkyl having 1 to 3 carbon atoms, which is optionally monosubstituted, suitable alkyl substituents being:

alkoxy, alkylthio, alkylamino or dialkylamino each having 1 or 2 carbon atoms in the individual alkyl moieties;

additionally represents straight-chain or branched halogenoalkyl having 1 to 3 carbon atoms and 1 to 7 identical or different halogen atoms—in particular fluorine, chlorine and/or bromine, or cycloalkyl having 3 to 6 carbon atoms;

$R^2$ represents hydrogen, hydroxyl, mercapto, amino, fluorine, chlorine, bromine or straight-chain or branched alkyl having 1 to 3 carbon atoms, which is optionally monosubstituted, suitable alkyl substituents being:

cyano and alkoxy, alkylthio, alkylamino or dialkylamino each having 1 or 2 carbon atoms in the individual alkyl moieties;

additionally represents straight-chain or branched halogenoalkyl having 1 to 3 carbon atoms and 1 to 7 identical or different halogen atoms—in particular fluorine, chlorine and/or bromine, additionally represents alkenyl or alkinyl each having 2 to 4 carbon atoms and each of which is straight-chain or branched, alkoxy, alkylthio, alkylsulphinyl or alkylsulphonyl each having 1 to 3 carbon atoms and each of which is straight-chain or branched, or cycloalkyl having 3 to 6 carbon atoms;

additionally represents phenylalkyl having 1 or 2 carbon atoms in the alkyl moiety, which is optionally monosubstituted or disubstituted in the phenyl moiety by identical or different substituents, suitable phenyl substituents being:

halogen, cyano, nitro, alkyl, alkoxy or alkylthio each having 1 or 2 carbon atoms, halogenoalkyl, halogenoalkoxy or halogenoalkylthio each having 1 or 2 carbon atoms and 1 to 5 identical or different halogen atoms—in particular fluorine, chlorine and/or bromine, alkoxycarbonyl or alkoximinoalkyl having 1 to 3 carbon atoms and phenyl which is optionally monosubstituted or disubstituted by identical or different fluorine, chlorine, bromine, methyl and/or ethyl substituents;

and additionally represents a radical

Het represents a heterocycle of the formula

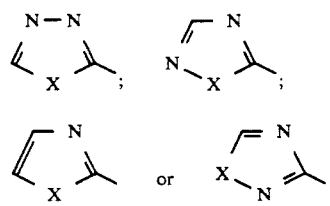

which is optionally monosubstituted or disubstituted by identical or different substituents, suitable substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino, alkanoylamino, halogenoalkylcarbonylamino or alkylaminocarbonylamino each having 1 to 4 carbon atoms in the individual alkyl moieties and optionally 1 to 7 identical or different halogen atoms—in particular fluorine, chlorine and/or bromine, and each of which is straight-chain or branched, alkenyl or alkinyl each having 2 to 4 carbon atoms and each of which is straight-chain or branched, straight-chain or branched alkylideneamino having 1 to 3 carbon atoms, halogenoalkyl, halogenoalkoxy, halogenoalkylthio, halogenoalkylsulphinyl or halogenoalkylsulphonyl each having 1 to 3 carbon atoms and 1 to 7 identical or different halogen atoms and each of which is straight-chain or branched, straight-chain or branched alkoxycarbonyl having 1 to 4 carbon atoms, cycloalkyl having 3 to 6 carbon atoms and phenyl, benzyl, phenylethyl, benzylideneamino or benzylaminocarbonylamino, each of which is optionally monosubstituted or disubstituted in the phenyl moiety by identical or different fluorine, chlorine, bromine, methyl, ethyl, methoxy, ethoxy and/or trifluoromethyl substituents and X represents oxygen, sulphur, an NH group an N-methyl group or an N-ethyl group, where R³ represents hydrogen or straight-chain or branched alkyl having 1 to 3 carbon atoms, which is optionally monosubstituted, suitable alkyl substituents being:

cyano, alkoxy, alkylthio, alkylamino or dialkylamino each having 1 or 2 carbon atoms in the individual alkyl moieties and phenyl which is optionally monosubstituted or disubstituted by identical or different fluorine, chlorine, bromine, methyl and/or ethyl substituents;

additionally represents straight-chain or branched halogenoalkyl having 1 to 3 carbon atoms and 1 to 7 identical or different halogen atoms—in particular fluorine, chlorine and/or bromine, additionally represents alkenyl or alkinyl each having 2 to 4 carbon atoms and each of which is straight-chain or branched, straight-chain or branched alkoxy having 1 to 3 carbon atoms or cycloalkyl having 3 to 6 carbon atoms and R⁴ represents straight-chain or branched alkyl having 1 to 3 carbon atoms, which is optionally monosubstituted, suitable alkyl substituents being:

cyano, alkoxy, alkylthio, alkylamino or dialkylamino each having 1 or 2 carbon atoms in the individual alkyl moieties and phenyl which is optionally monosubstituted or disubstituted by identical or different fluorine, chlorine, bromine, methyl and/or ethyl substituents;

additionally represents straight-chain or branched halogenoalkyl having 1 to 3 carbon atoms and 1 to 7 identical or different halogen atoms—in particular fluorine, chlorine and/or bromine, additionally represents alkenyl or alkinyl each having 2 to 4 carbon atoms and each of which is straight-chain or branched, straight-chain or branched alkoxy having 1 to 3 carbon atoms or cycloalkyl having 3 to 6 carbon atoms or R³ and R⁴, together with the nitrogen atom to which they are bonded, represent a 1-pyrrolidinyl, 1-piperidinyl, 1-perhydroazepinyl or 4-morpholinyl radical which is optionally monosubstituted or disubstituted by identical or different methyl and/or ethyl and/or methoxy substituents.

The following heterocyclyltriazolinones of the general formula (I) may be mentioned in detail in addition to the compounds mentioned in the preparation examples:

| R¹ | R² | Het |
|---|---|---|
| CH₃ | N(CH₃)₂ | 5-fluoro-2-methyl-1,3,4-thiadiazol-2-yl (F, S, N=N, CH₃) |
| CH₃ | N(CH₃)₂ | 5-chloro-2-methyl-1,3,4-thiadiazol-2-yl (Cl) |
| CH₃ | N(CH₃)₂ | 5-bromo-2-methyl-1,3,4-thiadiazol-2-yl (Br) |
| CH₃ | N(CH₃)₂ | 5-hydroxy-2-methyl-1,3,4-thiadiazol-2-yl (HO) |
| CH₃ | N(CH₃)₂ | 5-mercapto-2-methyl-1,3,4-thiadiazol-2-yl (HS) |
| C₂H₅ | N(CH₃)₂ | 5-amino-2-methyl-1,3,4-thiadiazol-2-yl (H₂N) |
| CH₃ | N(CH₃)₂ | 5-cyano-2-methyl-1,3,4-thiadiazol-2-yl (NC) |
| CH₃ | N(CH₃)₂ | 2,5-dimethyl-1,3,4-thiadiazol-2-yl (H₃C) |
| CH₃ | N(CH₃)₂ | 5-ethyl-2-methyl-1,3,4-thiadiazol-2-yl (H₅C₂) |
| CH₃ | N(CH₃)₂ | 5-methyl-2-methyl-1,3,4-thiadiazol-2-yl (H₃C) |
| CH₃ | N(CH₃)₂ | 5-cyclopropyl-2-methyl-1,3,4-thiadiazol-2-yl |
| CH₃ | N(CH₃)₂ | 5-cyclohexyl-2-methyl-1,3,4-thiadiazol-2-yl |
| CH₃ | N(CH₃)₂ | 5-cycloheptyl-2-methyl-1,3,4-thiadiazol-2-yl |
| CH₃ | N(CH₃)₂ | 5-benzyl-2-methyl-1,3,4-thiadiazol-2-yl (CH₂-Ph) |
| CH₃ | N(CH₃)₂ | 5-methoxy-2-methyl-1,3,4-thiadiazol-2-yl (H₃CO) |
| CH₃ | N(CH₃)₂ | 5-methylthio-2-methyl-1,3,4-thiadiazol-2-yl (H₃CS) |
| CH₃ | N(CH₃)₂ | 5-ethoxy-2-methyl-1,3,4-thiadiazol-2-yl (H₅C₂O) |
| CH₃ | N(CH₃)₂ | 5-methylsulfinyl-2-methyl-1,3,4-thiadiazol-2-yl (H₃C-S(O)) |
| CH₃ | N(CH₃)₂ | 5-methylsulfonyl-2-methyl-1,3,4-thiadiazol-2-yl (H₃C-S(O)₂) |
| CH₃ | N(CH₃)₂ | 5-ethylthio-2-methyl-1,3,4-thiadiazol-2-yl (H₅C₂-S) |
| CH₃ | N(CH₃)₂ | 5-ethylsulfinyl-2-methyl-1,3,4-thiadiazol-2-yl (H₅C₂-S(O)) |
| CH₃ | N(CH₃)₂ | 5-ethylsulfonyl-2-methyl-1,3,4-thiadiazol-2-yl (H₅C₂-S(O)₂) |
| CH₃ | N(CH₃)₂ | 5-(2-chlorophenyl)-2-methyl-1,3,4-thiadiazol-2-yl |
| CH₃ | N(CH₃)₂ | 5-(3-chlorophenyl)-2-methyl-1,3,4-thiadiazol-2-yl |
| CH₃ | -N(CH₃)(C₂H₅) | 5-trifluoromethyl-2-methyl-1,3,4-thiadiazol-2-yl (F₃C) |
| CH₃ | N(CH₃)₂ | 5-(4-chlorophenyl)-2-methyl-1,3,4-thiadiazol-2-yl |

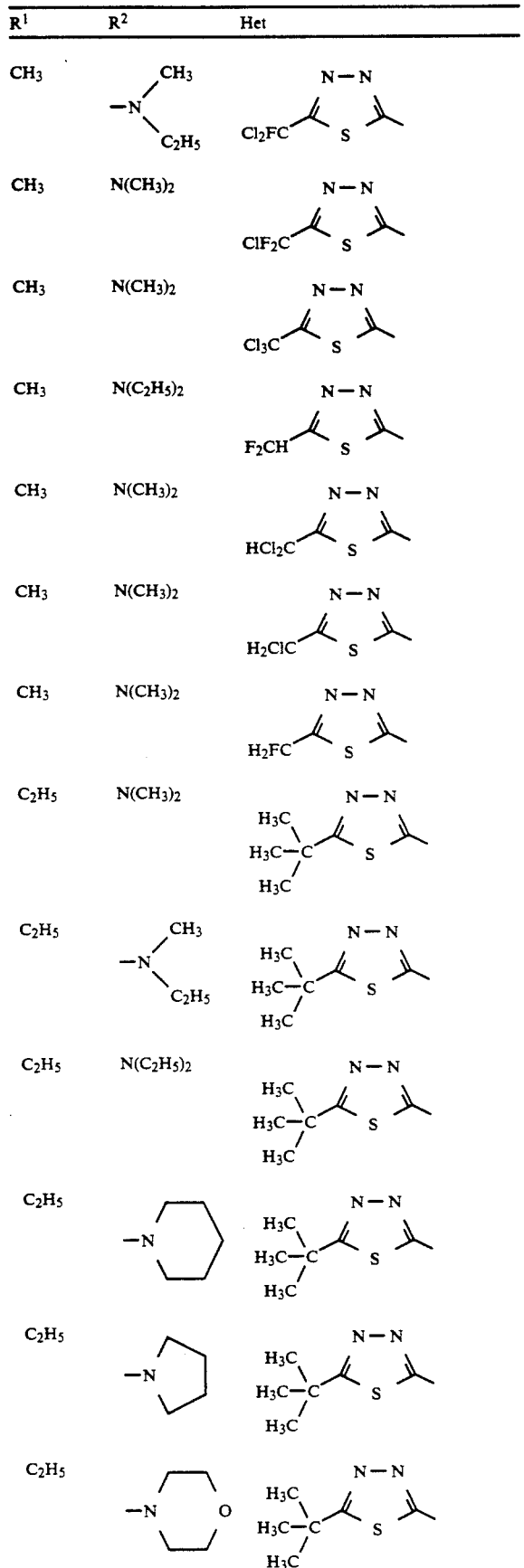
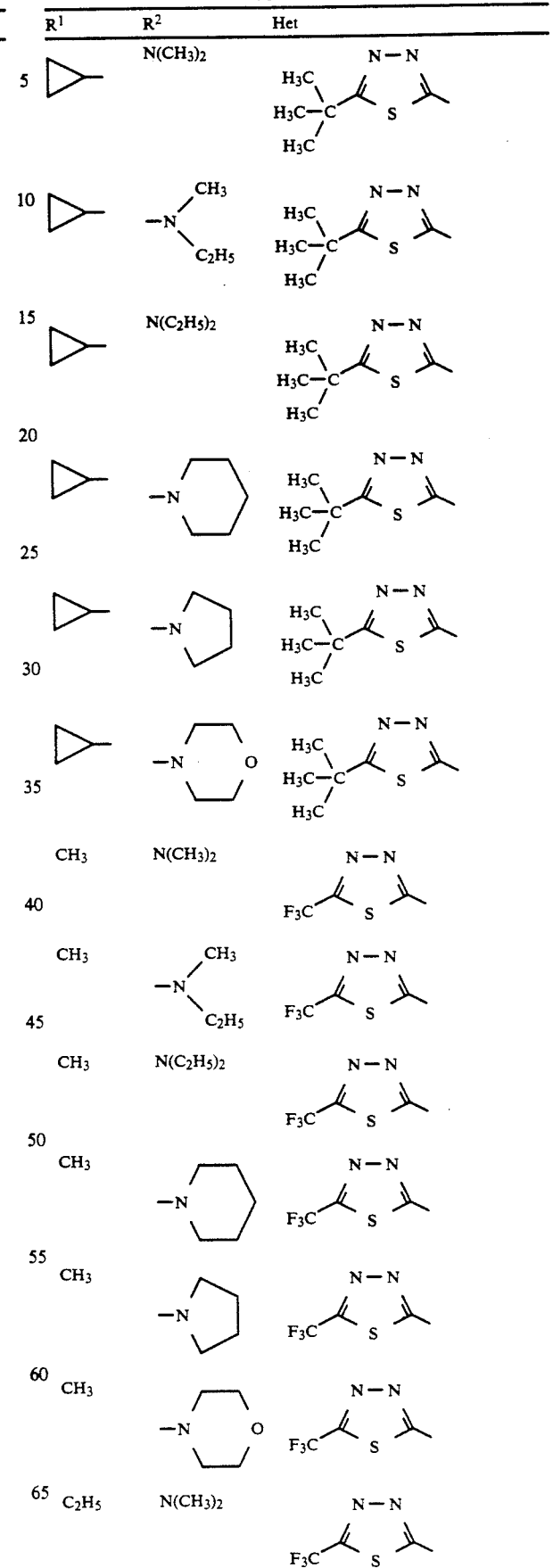

-continued

| R¹ | R² | Het |
|---|---|---|
| C₂H₅ | −N(CH₃)(C₂H₅) | 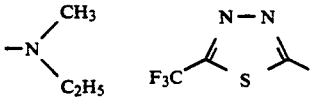 |
| C₂H₅ | N(C₂H₅)₂ | 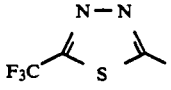 |
| C₂H₅ | −N(piperidine) | 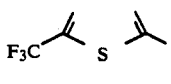 |
| C₂H₅ | −N(pyrrolidine) | 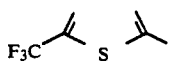 |
| C₂H₅ | −N(morpholine) | 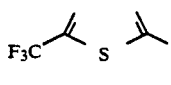 |
| CH₃ | −N(CH₃)(n-C₃H₇) | 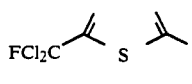 |
| CH₃ | N(C₂H₅)₂ | 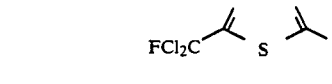 |
| CH₃ | −N(piperidine) | 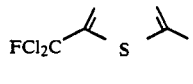 |
| CH₃ | −N(pyrrolidine) | 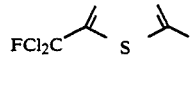 |
| CH₃ | −N(morpholine) | 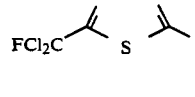 |
| C₂H₅ | N(CH₃)₂ | 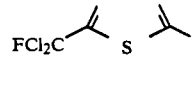 |
| C₂H₅ | N(C₂H₅)₂ | 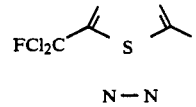 |
| C₂H₅ | −N(piperidine) | 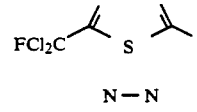 |
| C₂H₅ | −N(pyrrolidine) | 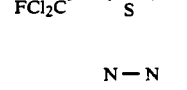 |

-continued

| R¹ | R² | Het |
|---|---|---|
| C₂H₅ | −N(morpholine) | 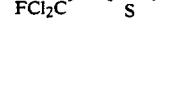 |
| CH₃ | −N(CH₃)(C₂H₅) | 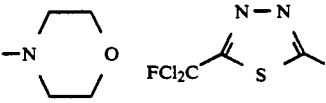 |
| CH₃ | −N(CH₃)(i-C₃H₇) | 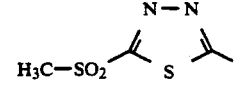 |
| CH₃ | N(C₂H₅)₂ | 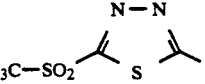 |
| CH₃ | −N(piperidine) | 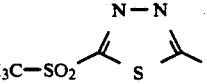 |
| CH₃ | −N(pyrrolidine) | 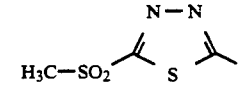 |
| CH₃ | −N(morpholine) | 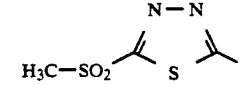 |
| C₂H₅ | N(CH₃)₂ | 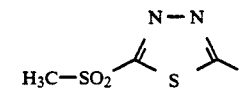 |
| C₂H₅ | −N(CH₃)(C₂H₅) | 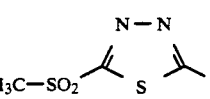 |
| C₂H₅ | N(C₂H₅)₂ | 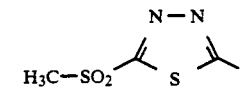 |
| C₂H₅ | −N(piperidine) | 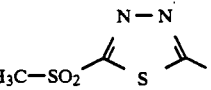 |
| C₂H₅ | −N(pyrrolidine) | 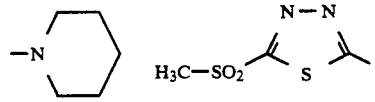 |
| C₂H₅ | −N(morpholine) | 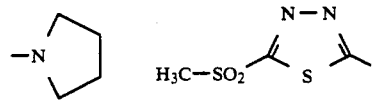 |

-continued

| R¹ | R² | Het |
|---|---|---|
| CH₃ | SCH₃ | 5-(tert-butyl)-1,3,4-thiadiazol-2-yl with 3-methyl (H₃C-C(CH₃)₂-C=N-N=C(CH₃)-S) |
| CH₃ | SCH₃ | 5-(trifluoromethyl)-3-methyl-1,3,4-thiadiazol-2-yl (F₃C-) |
| CH₃ | SCH₃ | 5-(dichlorofluoromethyl)-3-methyl-1,3,4-thiadiazol-2-yl (FCl₂C-) |
| CH₃ | SCH₃ | 5-(fluoromethyl)-3-methyl-1,3,4-thiadiazol-2-yl (H₂FC-) |
| CH₃ | SCH₃ | 5-(methylsulfonyl)-3-methyl-1,3,4-thiadiazol-2-yl (CH₃-SO₂-) |
| CH₃ | CH₃ | 5-(tert-butyl)-3-methyl-1,3,4-thiadiazol-2-yl |
| CH₃ | CH₃ | 5-(trifluoromethyl)-3-methyl-1,3,4-thiadiazol-2-yl |
| CH₃ | CH₃ | 5-(dichlorofluoromethyl)-3-methyl-1,3,4-thiadiazol-2-yl |
| CH₃ | CH₃ | 5-(fluoromethyl)-3-methyl-1,3,4-thiadiazol-2-yl |
| CH₃ | CH₃ | 5-(methylsulfonyl)-3-methyl-1,3,4-thiadiazol-2-yl |
| CH₃ | C₂H₅ | 5-(tert-butyl)-3-methyl-1,3,4-thiadiazol-2-yl |
| CH₃ | C₂H₅ | 5-(trifluoromethyl)-3-methyl-1,3,4-thiadiazol-2-yl |
| CH₃ | C₂H₅ | 5-(dichlorofluoromethyl)-3-methyl-1,3,4-thiadiazol-2-yl |
| CH₃ | C₂H₅ | 5-(fluoromethyl)-3-methyl-1,3,4-thiadiazol-2-yl |

-continued

| R¹ | R² | Het |
|---|---|---|
| CH₃ | C₂H₅ | 5-(methylsulfonyl)-3-methyl-1,3,4-thiadiazol-2-yl |
| CH₃ | cyclopropyl | 5-(tert-butyl)-3-methyl-1,3,4-thiadiazol-2-yl |
| CH₃ | cyclopropyl | 5-(trifluoromethyl)-3-methyl-1,3,4-thiadiazol-2-yl |
| CH₃ | cyclopropyl | 5-(dichlorofluoromethyl)-3-methyl-1,3,4-thiadiazol-2-yl |
| CH₃ | cyclopropyl | 5-(fluoromethyl)-3-methyl-1,3,4-thiadiazol-2-yl |
| CH₃ | cyclopropyl | 5-(methylsulfonyl)-3-methyl-1,3,4-thiadiazol-2-yl |
| CH₃ | CH₃O | 5-(tert-butyl)-3-methyl-1,3,4-thiadiazol-2-yl |
| CH₃ | CH₃O | 5-(trifluoromethyl)-3-methyl-1,3,4-thiadiazol-2-yl |
| CH₃ | CH₃O | 5-(dichlorofluoromethyl)-3-methyl-1,3,4-thiadiazol-2-yl |
| CH₃ | CH₃O | 5-(fluoromethyl)-3-methyl-1,3,4-thiadiazol-2-yl |
| CH₃ | CH₃O | 5-(methylsulfonyl)-3-methyl-1,3,4-thiadiazol-2-yl |
| CH₃ | NH-CH₃ | 5-(tert-butyl)-3-methyl-1,3,4-thiadiazol-2-yl |
| CH₃ | NH-CH₃ | 5-(trifluoromethyl)-3-methyl-1,3,4-thiadiazol-2-yl |
| CH₃ | NH-CH₃ | 5-(dichlorofluoromethyl)-3-methyl-1,3,4-thiadiazol-2-yl |

-continued

| R¹ | R² | Het |
|---|---|---|
| CH₃ | NH—CH₃ | 5-(difluoromethyl)-3-methyl-1,3,4-thiadiazol-2-yl |
| CH₃ | NH—CH₃ | 5-(methylsulfonyl)-3-methyl-1,3,4-thiadiazol-2-yl |
| CH₃ | C₂H₅O | 5-(1-methylpropyl)-3-methyl-1,3,4-thiadiazol-2-yl |
| CH₃ | C₂H₅O | 5-(trifluoromethyl)-3-methyl-1,3,4-thiadiazol-2-yl |
| CH₃ | C₂H₅O | 5-(chlorodifluoromethyl)-3-methyl-1,3,4-thiadiazol-2-yl |
| CH₃ | C₂H₅O | 5-(difluoromethyl)-3-methyl-1,3,4-thiadiazol-2-yl |
| CH₃ | C₂H₅O | 5-(methylsulfonyl)-3-methyl-1,3,4-thiadiazol-2-yl |
| CH₃ | N(CH₃)₂ | 5-(tert-butyl)-3-methyl-1,3,4-thiadiazol-2-yl |
| CH₃ | N(CH₃)₂ | 5-(methylsulfonyl)-3-methyl-1,3,4-oxadiazol-2-yl |
| CH₃ | N(CH₃)₂ | 5-(trifluoromethyl)-3-methyl-1,3,4-oxadiazol-2-yl |
| CH₃ | N(CH₃)₂ | 5-(tert-butyl)-3-methyl-1,3,4-thiadiazol-2-yl |
| CH₃ | N(CH₃)₂ | 5-(methylsulfonyl)-1,3-dimethyl-1,2,4-triazol-2-yl |
| CH₃ | N(CH₃)₂ | 5-(trifluoromethyl)-1,3-dimethyl-1,2,4-triazol-2-yl |

-continued

| R¹ | R² | Het |
|---|---|---|
| CH₃ | N(CH₃)₂ | 4-(tert-butyl)-3-methyl-1,2,5-thiadiazol-5-yl |
| CH₃ | N(CH₃)₂ | 4-(methylsulfonyl)-3-methyl-1,2,5-thiadiazol-5-yl |
| CH₃ | N(CH₃)₂ | 4-(trifluoromethyl)-3-methyl-1,2,5-thiadiazol-5-yl |
| CH₃ | N(CH₃)₂ | 4-(1-methylpropyl)-3-methyl-1,2,5-oxadiazol-5-yl |
| CH₃ | N(CH₃)₂ | 4-(methylsulfonyl)-3-methyl-1,2,5-oxadiazol-5-yl |
| CH₃ | N(CH₃)₂ | 4-(trifluoromethyl)-3-methyl-1,2,5-oxadiazol-5-yl |
| CH₃ | N(CH₃)₂ | 5-(1-methylpropyl)-1,3-dimethyl-1,2,4-triazol-2-yl |
| CH₃ | N(CH₃)₂ | 5-(methylsulfonyl)-1,3-dimethyl-1,2,4-triazol-2-yl |
| CH₃ | N(CH₃)₂ | 5-(trifluoromethyl)-1,3-dimethyl-1,2,4-triazol-2-yl |
| CH₃ | N(CH₃)₂ | 5-(1-methylpropyl)-3-methyl-1,2,4-thiadiazol-2-yl |

-continued

| R¹ | R² | Het |
|---|---|---|
| CH₃ | N(CH₃)₂ | 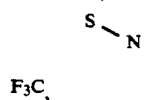 |
| CH₃ | N(CH₃)₂ | 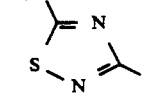 |
| CH₃ | N(CH₃)₂ | 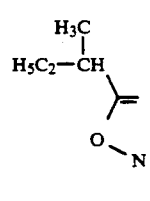 |
| CH₃ | N(CH₃)₂ | 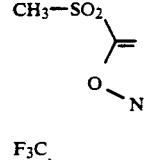 |
| CH₃ | N(CH₃)₂ | 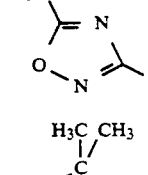 |
| CH₃ | N(CH₃)₂ | 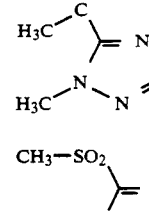 |
| CH₃ | N(CH₃)₂ | 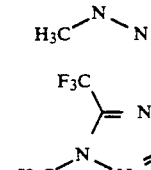 |
| CH₃ | N(CH₃)₂ | 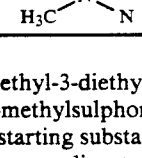 |

If, for example, 2-methyl-3-diethylamino-1,2,4-(1H)-triazolin-5-one and 2-methylsulphonyl-5-t-butyl-1,3,4-thiadiazole are used as starting substances, the course of reaction of the process according to the invention can be represented by the following equation:

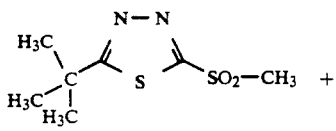

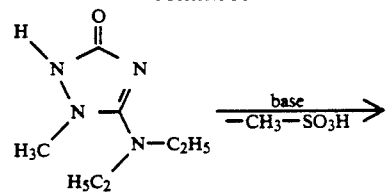

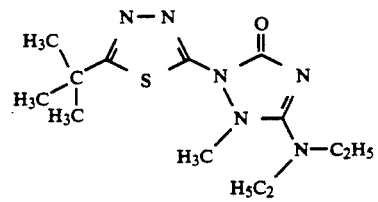

Formula (II) provides a general definition of the heterocycles required as starting substances for carrying out the process according to the invention. In this formula (II), Het preferably represents those radicals which have already been mentioned as preferred for these substituents in connection with the description of the compounds of the formula (I) according to the invention.

E represents a customary leaving radical, preferably halogen, in particular chlorine, bromine or iodine or alkylsulphonyl, alkylsulphonyloxy, alkoxysulphonyloxy or arylsulphonyloxy, each of which is optionally substituted, such as, in particular, methanesulphonyl, ethanesulphonyl, methanesulphonyloxy, trifluoromethanesulphonyloxy, methoxysulphonyloxy, ethoxysulphonyloxy or p-toluenesulphonyloxy.

The heterocycles of the formula (II) are known or obtainable in analogy to known processes (cf., for example, J. Med. Chem. 31, 906 [1988]; U.S. Pat. No. 4,454,147; U.S. Pat. No. 3,959,301; J. Prakt. Chem. 315, 611, [1973]; DE 40 31 158; DE 40 03 436).

Formula (III) provides a general definition of the triazolinones furthermore required as starting substances for carrying out the process according to the invention. In this formula (III), R¹ and R² preferably represent those radicals which have already been mentioned as preferred for these substituents in connection with the description of the compounds of the formula (I) according to the invention.

The triazolinones of the formula (III) are known or obtainable in analogy to known processes (cf., for example, DE 39 39 952; Bull. Chim. Soc. Fr. 1975, 1191; DE 24 07 304; DE 25 37 973; DE 24 23 765)

Suitable diluents for carrying out the process according to the invention are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate, or sulphoxides, such as dimethyl sulphoxide.

The process according to the invention can optionally be carried out in the presence of a suitable basic reaction auxiliary. Those which are suitable are all customary inorganic or organic bases. These include, for example, alkaline earth metal or alkali metal hydroxides, such as sodium hydroxide, calcium hydroxide, potassium hydroxide or alternatively ammonium hydroxide, alkali metal carbonates, such as sodium carbonate, potassium carbonate, potassium hydrogen carbonate, sodium hydrogen carbonate or ammonium carbonate, alkali metal or alkaline earth metal acetates, such as sodium acetate, potassium acetate, calcium acetate or ammonium acetate, and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

The process according to the invention can optionally also be carried out in a two-phase system, such as, for example, water/toluene or water/dichloromethane, if appropriate in the presence of a suitable phase transfer catalyst. Examples of such catalysts which may be mentioned are: tetrabutylammonium iodide, tetrabutylammonium bromide, tetrabutylammonium chloride, tributylmethylphosphonium bromide, trimethyl-$C_{13}/C_{15}$-alkylammonium chloride, trimethyl-$C_{13}/C_{15}$-alkylammonium bromide, dibenzyl-dimethyl-ammonium methylsulphate, dimethyl-$C_{12}/C_{14}$-alkyl-benzylammonium chloride, dimethyl-$C_{12}/C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)ethyl]-amine.

When carrying out the process according to the invention, the reaction temperatures can be varied within a relatively wide range. In general, the reaction is carried out at temperatures between $-20°$ C. and $+180°$ C., preferably at temperatures between $20°$ C. and $150°$ C.

The process according to the invention is customarily carried out under normal pressure. However, it is also possible to work at elevated or reduced pressure. To carry out the process according to the invention, 1.0 to 3.0 mol, preferably 1.0 to 1.5 mol, of triazolinone of the formula (III) and 1.0 to 5.0 mol, preferably 1.0 to 2.5 mol, of base as reaction auxiliary and if appropriate 0.001 to 2.0 mol, preferably 0.001 to 1.0 mol of phase transfer catalyst are in general employed per mol of heterocycle of the formula (II).

The reaction is carried out, and the reaction products are worked up and isolated by known processes (for this, also compare the preparation examples).

The final products of the formula (I) are purified with the aid of customary processes, for example by column chromatography or by recrystallisation.

Characterisation takes place with the aid of the melting point or, in the case of non-crystallising compounds, with the aid of the refractive index or of proton nuclear resonance spectroscopy ($^1$H-NMR).

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds according to the invention can be employed to particularly good effect for combating mono-and dicotyledon weeds in monocotyledon and dicotyledon crops such as, for example, wheat, maize or soya.

The active compounds can be converted into the customary formulations, such as solutions, emulsions, suspensions, powders, foams, pastes, granules, aerosols, natural and synthetic materials impregnated with active compound, and very fine capsules in polymeric substances.

These formulations are produced in a known manner, for example by mixing the active compounds with extenders, that is liquid solvents, liquified gases under pressure, and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural minerals such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latexes, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For controlling weeds, the active compounds according to the invention, as such or in the form of their formulations, can also be used as mixtures with known herbicides, finished formulations or tank mixes being possible.

Suitable herbicides for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon; carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxylamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amido-sulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiocarbamates such as, for example, butylate, cycloate, di-allate, EPTC, esprocarb, molinate, prosulfocarb, thiobencarb and tri-allate; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

A mixture with other known active compounds, such as fungicides, insecticides, acaricides, nematicides, bird repellants, plant nutrients and agents which improve soil structure, is also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied both before and after emergence of the plants.

They can also be incorporated into the soil before sowing.

The amount of active compound used can vary within a relatively wide range. It depends essentially on the nature of the desired effect. In general, the amounts used are between 0.001 and 10 kg of active compound per hectare of soil surface, preferably between 0.005 and 5 kg per ha.

The preparation and use of the active compounds according to the invention can be seen from the following examples.

PREPARATION EXAMPLES

Example 1

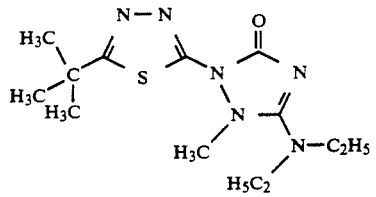

2.76 g (0.02 mol) of potassium carbonate is added to 1.7 g (0.01 mol) of 3-diethylamino-2-methyl-1,2,4-(1H)-triazolin-5-one (preparation analogously to DE 39 39 952) and 2.2 g (0.01 mol) of 2-methylsulphonyl-5-t-butyl-1,3,4-thiadiazole (preparation analogously to DE 40 03 436 or DE 34 22 861) in 50 ml of dimethylformamide and the mixture is heated at 90° C. for 20 hours. For working up, the cooled reaction mixture is poured into water, acidifed with dilute hydrochloric acid and extracted twice with dichloromethane. The combined organic phases are washed three times with water, dried over magnesium sulphate and concentrated in vacuo. The residue is made to crystallise by covering with a layer of ether/hexane (1:1) and the crystals are filtered off with suction.

1.1 g (35% of theory) of 1-(5-t-butyl-1,3,4-thiadiazol-2-yl)-3-diethylamino-2-methyl-1,2,4-(1H)-triazolin-5-one of melting point 93° C. are obtained.

The following heterocyclyltriazolinones of the general formula (I):

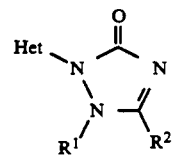
(I)

are obtained in a corresponding manner and in accordance with the general instructions for preparation.

| Ex. No. | R¹ | R² | Het | Physical properties |
|---|---|---|---|---|
| 2 | CH₃ | N(CH₃)₂ | H₂N–[N—N, S]– | m.p. 208° C. |
| 3 | CH₃ | N(CH₃)₂ | t-C₄H₉—NH—CO—NH–[N—N, S]– | m.p. >250° C. |
| 4 | CH₃ | N(CH₃)₂ | i-C₃H₇—NH—CO—NH–[N, N, S]– | m.p. >260° C. |
| 5 | CH₃ | N(CH₃)₂ | CH₃—CO—NH–[N, N, S]– | m.p. >260° C. |
| 6 | CH₃ | N(CH₃)₂ | CF₃—CO—NH–[N, N, S]– | m.p. >260° C. |
| 7 | CH₃ | N(CH₃)₂ | H₅C₆—CH=N–[N, N, S]– | m.p. 206° C. |
| 8 | CH₃ | N(CH₃)₂ | i-C₃H₇—CO—NH–[N, N, S]– | m.p. 252° C. |
| 9 | CH₃ | N(CH₃)₂ | H₂ClC—C(CH₃)₂—CO—NH–[N, N, S]– | m.p. 218° C. |
| 10 | CH₃ | N(CH₃)₂ | C₆H₅—CH(CH₃)—NH—CO—NH–[N, N, S]– | m.p. >260° C. |
| 11 | CH₃ | N(CH₃)₂ | NC, Cl –[N, S]– | m.p. 174° C. |

-continued
| Ex. No. | R¹ | R² | Het | Physical properties |
|---|---|---|---|---|
| 12 | CH₃ | N(C₂H₅)₂ | 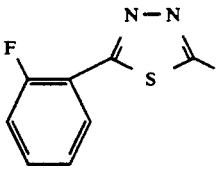 | m.p. 151° C. |
| 13 | CH₃ | N(C₂H₅)₂ | 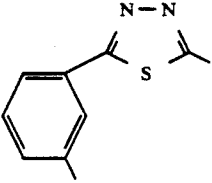 | m.p. 110° C. |
| 14 | CH₃ | —N(CH₃)(C₂H₅) | 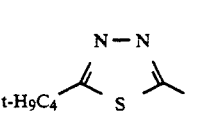 | m.p. 68° C. |
| 15 | CH₃ | —N(CH₃)(C₂H₅) | 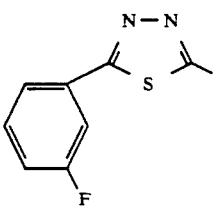 | m.p. 140° C. |
| 16 | CH₃ | piperidinyl | 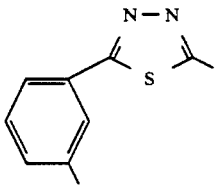 | m.p. 197° C. |
| 17 | CH₃ | pyrrolidinyl | 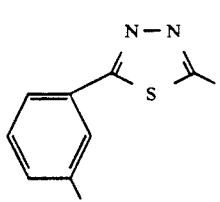 | m.p. 224° C. |
| 18 | CH₃ | N(C₂H₅)₂ | 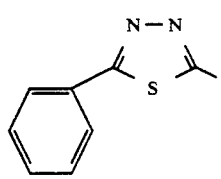 | m.p. 102° C. |
| 19 | CH₃ | —N(CH₃)(C₂H₅) | 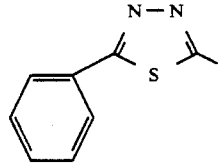 | m.p. 127° C. |

-continued

| Ex. No. | R¹ | R² | Het | Physical properties |
|---|---|---|---|---|
| 20 | CH₃ | piperidin-1-yl | 5-phenyl-2-isopropylidene-1,3,4-thiadiazol-3(2H)-yl | m.p. 208° C. |
| 21 | CH₃ | piperidin-1-yl | 5-(2-fluorophenyl)-2-isopropylidene-1,3,4-thiadiazol-3(2H)-yl | m.p. 201° C. |
| 22 | CH₃ | pyrrolidin-1-yl | 5-(2-fluorophenyl)-2-isopropylidene-1,3,4-thiadiazol-3(2H)-yl | m.p. 241° C. |
| 23 | CH₃ | pyrrolidin-1-yl | 5-phenyl-2-isopropylidene-1,3,4-thiadiazol-3(2H)-yl | m.p. 207° C. |
| 24 | CH₃ | morpholin-4-yl | 5-phenyl-2-isopropylidene-1,3,4-thiadiazol-3(2H)-yl | m.p. 265° C. |
| 25 | CH₃ | morpholin-4-yl | 5-(2-fluorophenyl)-2-isopropylidene-1,3,4-thiadiazol-3(2H)-yl | m.p. 267° C. |
| 26 | CH₃ | morpholin-4-yl | 5-(3-fluorophenyl)-2-isopropylidene-1,3,4-thiadiazol-3(2H)-yl | m.p. 269° C. |
| 27 | CH₃ | piperidin-1-yl | 5-tert-butyl-2-isopropylidene-1,3,4-thiadiazol-3(2H)-yl (t-H₉C₄) | m.p. 185° C. |
| 28 | CH₃ | morpholin-4-yl | 5-tert-butyl-2-isopropylidene-1,3,4-thiadiazol-3(2H)-yl (t-H₉C₄) | m.p. 228° C. |

-continued

| Ex. No. | R¹ | R² | Het | Physical properties |
|---|---|---|---|---|
| 29 | CH₃ | −N(CH₃)(n-C₃H₇) | t-H₉C₄−⟨N=N, S⟩−CH₃ | m.p. 46° C. |
| 30 | CH₃ | −N(i-C₃H₇)₂ | t-H₉C₄−⟨N=N, S⟩−CH₃ | m.p. 155° C. |
| 31 | CH₃ | −N(CH₃)(i-C₃H₇) | t-H₉C₄−⟨N=N, S⟩−CH₃ | m.p. 32° C. |
| 32 | CH₃ | −N(n-C₃H₇)(C₂H₅) | t-H₉C₄−⟨N=N, S⟩−CH₃ | m.p. 82° C. |
| 33 | CH₃ | −N(CH₃)(n-C₄H₉) | t-H₉C₄−⟨N=N, S⟩−CH₃ | m.p. 59° C. |
| 34 | CH₃ | N(CH₃)₂ | t-H₉C₄−⟨N=N, S⟩−CH₃ | $n_D^{20} = 1.5075$ |
| 35 | CH₃ | N(CH₃)₂ | s-H₉C₄−⟨N=N, S⟩−CH₃ | $n_D^{20} = 1.5165$ |
| 36 | CH₃ | −N(CH₃)(C₂H₅) | s-H₉C₄−⟨N=N, S⟩−CH₃ | $n_D^{20} = 1.5040$ |
| 37 | CH₃ | N(CH₃)₂ | t-H₉C₄−thiazole−CH₃ | m.p. 60° C. |
| 38 | CH₃ | −N(CH₃)(C₂H₅) | t-H₉C₄−thiazole−CH₃ | m.p. 70° C. |
| 39 | CH₃ | N(CH₃)₂ | F₃C−⟨N=N, N(CH₃)⟩−CH₃ | m.p. 63° C. |
| 40 | CH₃ | N(CH₃)₂ | FCl₂C−⟨N=N, S⟩−CH₃ | m.p. 115° C. |
| 41 | CH₃ | N(CH₃)₂ | HF₂C−⟨N=N, S⟩−CH₃ | m.p. 137° C. |
| 42 | CH₃ | N(CH₃)₂ | H₂N−CO−⟨N=N, S⟩−CH₃ | m.p. >300° C. |

-continued

| Ex. No. | R¹ | R² | Het | Physical properties |
|---|---|---|---|---|
| 43 | CH₃ | −N(CH₃)(C₂H₅) | 5-(H₂N−CO)-3-methyl-1,3,4-thiadiazol-2-yl | m.p. 190° C. |
| 44 | CH₃ | N(CH₃)₂ | 3-(F₃C)-5-methyl-1,2,4-thiadiazol-yl | m.p. 190° C. |
| 45 | CH₃ | −N(CH₃)(C₂H₅) | 5-(HF₂C)-3-methyl-1,3,4-thiadiazol-2-yl | wax |
| 46 | CH₃ | N(CH₃)₂ | 5-(n-C₃H₇)-3-methyl-1,3,4-thiadiazol-2-yl | m.p. 63° C. |
| 47 | CH₃ | N(CH₃)₂ | 5-(i-C₄H₉)-3-methyl-1,3,4-thiadiazol-2-yl | m.p. 98° C. |
| 48 | CH₃ | N(CH₃)₂ | 5-cyclohexyl-3-methyl-1,3,4-thiadiazol-2-yl | m.p. 85° C. |
| 49 | CH₃ | N(CH₃)₂ | 5-(i-C₃H₇)-3-methyl-1,3,4-thiadiazol-2-yl | m.p. 57° C. |
| 50 | CH₃ | N(CH₃)₂ | 5-(C₆H₅−CH(CH₃))-3-methyl-1,3,4-thiadiazol-2-yl | wax |
| 51 | CH₃ | N(CH₃)₂ | 5-cyclopentyl-3-methyl-1,3,4-thiadiazol-2-yl | m.p. 65° C. |
| 52 | CH₃ | N(CH₃)₂ | 5-cyclobutyl-3-methyl-1,3,4-thiadiazol-2-yl | m.p. 105° C. |
| 53 | CH₃ | N(CH₃)₂ | 5-(n-C₄H₉)-3-methyl-1,3,4-thiadiazol-2-yl | m.p. 40° C. |
| 54 | CH₃ | N(CH₃)₂ | 5-(t-C₄H₉−CH₂)-3-methyl-1,3,4-thiadiazol-2-yl | m.p. 127° C. |
| 55 | CH₃ | CH₃ | 5-(t-C₄H₉)-3-methyl-1,3,4-thiadiazol-2-yl | m.p. 45° C. |

USE EXAMPLES

In the following use examples, the compound shown below was employed as a comparison substance:

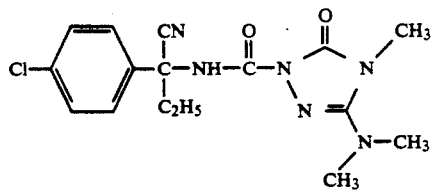

1-{1-[1-(4-chlorophenyl)-1-cyano]-propyl-aminocarbonyl]}-3-dimethylamino-4-methyl-1,2,4-triazolin-5-one. (Known from EP 283 876)

EXAMPLE A

Pre-emergence test

| Solvent: | 5 parts by weight of acetone |
|---|---|
| Emulsifier: | 1 part by weight of alkylaryl polyglycol ether |

To produce a suitable preparation of active compound, one part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:

0% = no action (like untreated control)
100% = total destruction

In this test, for example, the compounds according to Preparation Examples 1, 14, 31, 41 and 45 show a clearly superior activity with comparable crop plant selectivity compared to the prior art.

EXAMPLE B

Post-emergence test

| Solvent: | 5 parts by weight of acetone |
|---|---|
| Emulsifier: | 1 part by weight of alkylaryl polyglycol ether |

To produce a suitable preparation of active compound, one part by weight of active compound is mixed with the stated amount of solvent, the stated amount of emulsifier is added and the concentrate is diluted with water to the desired concentration.

Test plants which have a height of 5 to 15 cm are sprayed with the preparation of the active compound in such a way as to apply the amounts of active compound desired in each case per unit area. After three weeks, the degree of damage to the plants is rated in % damage in comparison to the development of the untreated control.

The figures denote:

0% = no action (like untreated control)
100% = total destruction

In this test, for example, the compounds according to Preparation Examples 1, 13, 14, 28, 29, 31, 34 and 41 show a clearly superior activity just as in the crop plant selectivity compared to the prior art.

It will be understood that the specification and examples are illustrative but not limitative of the present invention and that other embodiments within the spirit and scope of the invention will suggest themselves to those skilled in the art.

What is claimed is:

1. A heterocyclyltriazolinone of the general formula (I)

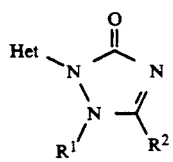

wherein
R¹ represents hydrogen, or represents alkyl or cycloalkyl, each of which is optionally substituted,
R² represents hydrogen, hydroxyl, mercapto or halogen or represents alkyl, alkenyl, alkinyl, cycloalkyl, alkoxy, alkylthio, alkylsulphinyl, alkylsulphonyl, arylalkyl, amino or heterocyclyl, each of which is optionally substituted, and
Het represents an optionally substituted heterocycle of the formula

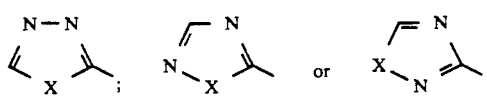

in which
X in each case represents oxygen, sulphur, an NH group or an N-alkyl group.

2. A heterocyclyltriazolinone of the general formula (I) according to claim 1, wherein
R¹ represents hydrogen, or straight-chain or branched alkyl having 1 to 6 carbon atoms, which is optionally monosubstituted or polysubstituted by identical or different substituents, suitable alkyl substituents being:
halogen, or alkoxy, alkylthio, alkylamino or dialkylamino each having 1 to 4 carbon atoms in the individual alkyl moieties and each of which is straight-chain or branched, and
additionally represents cycloalkyl having 3 to 8 carbon atoms;
R² represents hydrogen, hydroxyl, mercapto, amino, halogen or straight-chain or branched alkyl having 1 to 6 carbon atoms, which is optionally monosubstituted or polysubstituted by identical or different substituents, suitable alkyl substituents being:
halogen, cyano, or alkoxy, alkylthio, alkylamino or dialkylamino each having 1 to 4 carbon atoms in the individual alkyl moieties and each of which is straight-chain or branched,
additionally represents alkenyl or alkinyl each having 2 to 6 carbon atoms and each of which is straight-chain or branched, alkoxy, alkylthio, alkylsulphinyl or alkylsulphonyl each having 1 to 6 carbon atoms and each of which is straight-chain or branched, or cycloalkyl having 3 to 8 carbon atoms;

additionally represents arylalkyl having 6 to 10 carbon atoms in the aryl moiety and 1 to 6 carbon atoms in the straight-chain or branched alkyl moiety which is optionally monosubstituted or polysubstituted in the aryl moiety by identical or different substituents, suitable aryl substituents being:

halogen, cyano, nitro, or alkyl, alkoxy or alkylthio each having 1 to 4 carbon atoms and each of which is straight-chain or branched, halogenoalkyl, halogenoalkoxy or halogenoalkylthio each having 1 to 4 carbon atoms and 1 to 9 identical or different halogen atoms and each of which is straight-chain or branched, alkoxycarbonyl or alkoximinoalkyl each having 1 to 4 carbon atoms in the individual alkyl moieties and each of which is straight-chain or branched, and phenyl which is optionally monosubstituted or polysubstituted by identical or different halogen substituents and/or straight-chain or branched alkyl substituents having 1 to 4 carbon atoms;

and additionally represents a radical

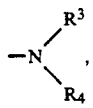

Het represents a heterocycle of the formula

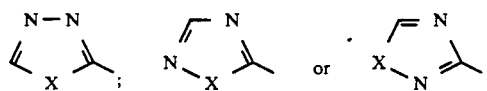

which is optionally monosubstituted or polysubstituted by identical or different substituents, suitable substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino, alkanoylamino; halogenoalkylcarbonylamino or alkylaminocarbonylamino each having 1 to 8 carbon atoms in the individual alkyl moieties and optionally 1 to 13 identical or different halogen atoms and each of which is straight-chain or branched, alkenyl or alkinyl each having 2 to 6 carbon atoms and each of which is straight-chain or branched, straight-chain or branched alkylideneamino having 1 to 6 carbon atoms, halogenoalkyl, halogenoalkoxy, halogenoalkylthio, halogenoalkylsulphinyl or halogenoalkylsulphonyl each having 1 to 6 carbon atoms and 1 to 13 identical or different halogen atoms and each of which is straight-chain or branched, straight-chain or branched alkoxycarbonyl having 1 to 7 carbon atoms, cycloalkyl having 3 to 8 carbon atoms and aryl, arylalkyl, arylalkylideneamino or arylalkylaminocarbonylamino each having 6 to 10 carbon atoms in the aryl moiety and optionally 1 to 4 carbon atoms in the straight-chain or branched alkyl moiety and each of which is optionally monosubstituted or polysubstituted in the aryl moiety by identical or different halogen substituents and/or straight-chain or branched alkyl and/or alkoxy substituents each having 1 to 4 carbon atoms and/or halogenoalkyl substituents having 1 to 4 carbon atoms and 1 to 9 identical or different halogen atoms, and X in each case represents oxygen, sulphur, an NH group or a straight-chain or branched N-alkyl group having 1 to 8 carbon atoms, $R^3$ represents hydrogen or straight-chain or branched alkyl having 1 to 6 carbon atoms, which is optionally monosubstituted or polysubstituted by identical or different substituents, suitable alkyl substituents being:

halogen, cyano, or alkoxy, alkylthio, alkylamino or dialkylamino each having 1 to 4 carbon atoms in the individual alkyl moieties and each of which is straight-chain or branched, and phenyl which is optionally monosubstituted or polysubstituted by identical or different halogen substituents and/or straight-chain or branched alkyl substituents having 1 to 4 carbon atoms;

additionally represents alkenyl or alkinyl each having 2 to 6 carbon atoms and each of which is straight-chain or branched, straight-chain or branched alkoxy having 1 to 6 carbon atoms or cycloalkyl having 3 to 8 carbon atoms and $R^4$ represents straight-chain or branched alkyl having 1 to 6 carbon atoms, which is optionally monosubstituted or polysubstituted by identical or different substituents, suitable alkyl substituents being:

halogen, cyano, or alkoxy, alkylthio, alkylamino or dialkylamino each having 1 to 4 carbon atoms in the individual alkyl moieties and each of which is straight-chain or branched, and phenyl which is optionally monosubstituted or polysubstituted by identical or different halogen substituents and/or straight-chain or branched alkyl substituents having 1 to 4 carbon atoms;

additionally represents alkenyl or alkinyl each having 2 to 6 carbon atoms and each of which is straight-chain or branched, straight-chain or branched alkoxy having 1 to 6 carbon atoms or cycloalkyl having 3 to 8 carbon atoms or $R^3$ and $R^4$, together with the nitrogen atom to which they are bonded, represent a saturated or unsaturated heterocycle which can optionally contain 1 to 3 further heteroatoms—in particular nitrogen, oxygen and/or sulphur, and which is optionally monosubstituted or polysubstituted by identical or different substituents, suitable heterocyclyl substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino or alkanoylamino; halogenoalkylcarbonylamino or alkylaminocarbonylamino each having 1 to 8 carbon atoms in the individual alkyl moieties and optionally 1 to 13 identical or different halogen atoms and each of which is straight-chain or branched, alkenyl or alkinyl each having 2 to 6 carbon atoms and each of which is straight-chain or branched, straight-chain or branched alkylideneamino having 1 to 6 carbon atoms, halogenoalkyl, halogenoalkoxy, halogenoalkylthio, halogenoalkylsulphinyl or halogenoalkylsulphonyl each having 1 to 6 carbon atoms and 1 to 13 identical or different halogen atoms and each of which is straight-chain or branched, straight-chain or branched alkoxycarbonyl having 1 to 7 carbon atoms, cycloalkyl having 3 to 8 carbon atoms and aryl, arylalkyl, arylalkylideneamino or arylalkylaminocarbonylamino each having 6 to 10 carbon atoms in the aryl moiety and optionally 1 to 4 carbon atoms in the straight-chain or branched alkyl moiety and each of which is optionally monosubstituted or polysubstituted in the aryl moiety by identical or different halogen substituents and/or straight-chain or branched alkyl and/or alkoxy substituents each having 1 to 4 carbon atoms and/or halogenoalkyl substituents having 1 to 4 carbon atoms and 1 to 9 identical or different halogen atoms.

3. A heterocyclyltriazolinone of the general formula (I) according to claim 1, wherein $R^1$ represents hydrogen, or straight-chain or branched alkyl having 1 to 4 carbon atoms, which is optionally monosubstituted to disubstituted by identical or different substituents, suitable alkyl substituents being:

alkoxy, alkylthio, alkylamino or dialkylamino each having 1 to 3 carbon atoms in the individual alkyl moieties and each of which is straight-chain or branched;

additionally represents straight-chain or branched halogenoalkyl having 1 to 4 carbon atoms and 1 to 9 identical or different halogen atoms—in particular fluorine, chlorine and/or bromine, additionally represents cycloalkyl having 3 to 7 carbon atoms;

$R^2$ represents hydrogen, hydroxyl, mercapto, amino, halogen or straight-chain or branched alkyl having 1 to 4 carbon atoms, which is optionally monosubstituted or disubstituted by identical or different substituents, suitable alkyl substituents being:

cyano, or alkoxy, alkylthio, alkylamino or dialkylamino each having 1 to 3 carbon atoms in the individual alkyl moieties and each of which is straight-chain or branched, additionally represents straight-chain or branched halogenoalkyl having 1 to 4 carbon atoms and 1 to 9 identical or different halogen atoms—in particular fluorine, chlorine and/or bromine, additionally represents alkenyl or alkinyl each having 2 to 5 carbon atoms and each of which is straight-chain or branched, alkoxy, alkylthio, alkylsulphinyl or alkylsulphonyl each having 1 to 4 carbon atoms and each of which is straight-chain or branched, or cycloalkyl having 3 to 7 carbon atoms;

additionally represents arylalkyl having 6 or 10 carbon atoms in the aryl moiety and 1 to 4 carbon atoms in the straight-chain or branched alkyl moiety, which is optionally monosubstituted to trisubstituted in the aryl moiety by identical or different substituents, suitable aryl substituents being:

halogen, cyano, nitro, or alkyl, alkoxy or alkylthio each having 1 to 3 carbon atoms and each of which is straight-chain or branched, halogenoalkyl, halogenoalkoxy or halogenoalkylthio each having 1 to 3 carbon atoms and 1 to 7 identical or different halogen atoms and each of which is straight-chain or branched, alkoxycarbonyl or alkoximinoalkyl each having 1 to 3 carbon atoms in the individual alkyl moieties and each of which is straight-chain or branched, and phenyl which is optionally monosubstituted to trisubstituted by identical or different halogen substituents and/or straight-chain or branched alkyl substituents having 1 to 3 carbon atoms;

and additionally represents a radical

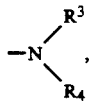

Het represents a heterocycle of the formula

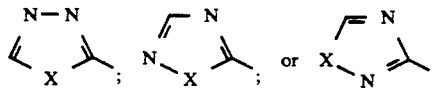

which is optionally monosubstituted to disubstituted by identical or different substituents, suitable substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino, alkanoylamino, halogenoalkylcarbonylamino or alkylaminocarbonylamino each having 1 to 6 carbon atoms in the individual alkyl moieties and optionally 1 to 13 identical or different halogen atoms—in particular fluorine, chlorine and/or bromine, and each of which is straight-chain or branched, alkenyl or alkinyl each having 2 to 5 carbon atoms and each of which is straight-chain or branched, straight-chain or branched alkylideneamino having 1 to 4 carbon atoms, halogenoalkyl, halogenoalkoxy, halogenoalkylthio, halogenoalkylsulphinyl or halogenoalkylsulphonyl each having 1 to 4 carbon atoms and 1 to 9 identical or different halogen atoms and each of which is straight-chain or branched, straight-chain or branched alkoxycarbonyl having 1 to 5 carbon atoms, cycloalkyl having 3 to 7 carbon atoms and aryl, arylalkyl, arylalkylideneamino or arylalkylaminocarbonylamino each having 6 or 10 carbon atoms in the aryl moiety and optionally 1 to 3 carbon atoms in the straight-chain or branched alkyl moiety and each of which is optionally monosubstituted to trisubstituted in the aryl moiety by identical or different halogen substituents and/or straight-chain or branched alkyl and/or alkoxy substituents each having 1 to 3 carbon atoms and/or halogenoalkyl substituents having 1 to 3 carbon atoms and 1 to 7 identical or different halogen atoms and X in each case represents oxygen, sulphur, an NH group or a straight-chain or branched N-alkyl group having 1 to 6 carbon atoms, $R^3$ represents hydrogen or straight-chain or branched alkyl having 1 to 4 carbon atoms, which is optionally monosubstituted to disubstituted by identical or different substituents, suitable alkyl substituents being:

cyano, or alkoxy, alkylthio, alkylamino or dialkylamino each having 1 to 3 carbon atoms in the individual alkyl moieties and each of which is straight-chain or branched, and phenyl which is optionally monosubstituted to trisubstituted by identical or different halogen substituents and/or straight-chain or branched alkyl substituents having 1 to 3 carbon atoms;

additionally represents straight-chain or branched halogenoalkyl having 1 to 4 carbon atoms and 1 to 9 identical or different halogen atoms—in particular fluorine, chlorine and/or bromine, additionally represents alkenyl or alkinyl each having 2 to 5 carbon atoms and each of which is straight-chain or branched, straight-chain or branched alkoxy having 1 to 4 carbon atoms or cycloalkyl having 3 to 7 carbon atoms and $R^4$ represents straight-chain or branched alkyl having 1 to 4 carbon atoms, which is optionally monosubstituted or disubstituted by identical or different substituents, suitable alkyl substituents being:

cyano, or alkoxy, alkylthio, alkylamino or dialkylamino each having 1 to 3 carbon atoms in the individual alkyl moieties and each of which is straight-chain or branched, and phenyl which is optionally monosubstituted to trisubstituted by identical or different halogen substituents and/or straight-chain or branched alkyl substituents having 1 to 3 carbon atoms;

additionally represents straight-chain or branched halogenoalkyl having 1 to 4 carbon atoms and 1 to 9 identical or different halogen atoms—in particular fluorine, chlorine and/or bromine, additionally represents alkenyl or alkinyl each having 2 to 5 carbon atoms and each of which is straight-chain or branched, straight-chain or branched alkoxy having 1 to 4 carbon atoms or cycloalkyl having 3 to 7 carbon atoms or $R^3$ and $R^4$, together with the nitrogen atom to which they are bonded, represent a saturated five- to seven-membered, monocyclic heterocycle which is optionally monosubstituted or disubstituted by identical or different substituents and which can optionally contain 1 or 2 further heteroatoms—in particular nitrogen, oxygen and/or sulphur, suitable heterocyclyl substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino, alkanoylamino, halogenoalkylcarbonylamino or alkylaminocarbonylamino each having 1 to 6 carbon atoms in the individual alkyl moieties and optionally 1 to 13 identical or different halogen atoms—in particular fluorine, chlorine and/or bromine, and each of which is straight-chain or branched, alkenyl or alkinyl each having 2 to 5 carbon atoms and each of which is straight-chain or branched, straight-chain or branched alkylideneamino having 1 to 4 carbon atoms, halogenoalkyl, halogenoalkoxy, halogenoalkylthio, halogenoalkylsulphinyl or halogenoalkylsulphonyl each having 1 to 4 carbon atoms and 1 to 9 identical or different halogen atoms and each of which is straight-chain or branched, straight-chain or branched alkoxycarbonyl having 1 to 5 carbon atoms, cycloalkyl having 3 to 7 carbon atoms and aryl, arylalkyl, arylalkylideneamino or arylalkylaminocarbonylamino each having 6 or 10 carbon atoms in the aryl moiety and optionally 1 to 3 carbon atoms in the straight-chain or branched alkyl moiety and each of which is optionally monosubstituted to trisubstituted in the aryl moiety by identical or different halogen substituents and/or straight-chain or branched alkyl and/or alkoxy substituents each having 1 to 3 carbon atoms and/or halogenoalkyl substituents having 1 to 3 carbon atoms and 1 to 7 identical or different halogen atoms.

4. A heterocyclyltriazolinone of the general formula (I) according to claim 1, wherein $R^1$ represents hydrogen, or straight-chain or branched alkyl having 1 to 3 carbon atoms, which is optionally monosubstituted, suitable alkyl substituents being:

alkoxy, alkylthio, alkylamino or dialkylamino each having 1 or 2 carbon atoms in the individual alkyl moieties;

additionally represents straight-chain or branched halogenoalkyl having 1 to 3 carbon atoms and 1 to 7 identical or different halogen atoms—in particular fluorine, chlorine and/or bromine, or cycloalkyl having 3 to 6 carbon atoms;

$R^2$ represents hydrogen, hydroxyl, mercapto, amino, fluorine, chlorine, bromine or straight-chain or branched alkyl having 1 to 3 carbon atoms, which is optionally monosubstituted, suitable alkyl substituents being:

cyano and alkoxy, alkylthio, alkylamino or dialkylamino each having 1 or 2 carbon atoms in the individual alkyl moieties;

additionally represents straight-chain or branched halogenoalkyl having 1 to 3 carbon atoms and 1 to 7 identical or different halogen atoms—in particular fluorine, chlorine and/or bromine, additionally represents alkenyl or alkinyl each having 2 to 4 carbon atoms and each of which is straight-chain or branched, alkoxy, alkylthio, alkylsulphinyl or alkylsulphonyl each having 1 to 3 carbon atoms and each of which is straight-chain or branched, or cycloalkyl having 3 to 6 carbon atoms;

additionally represents phenylalkyl having 1 or 2 carbon atoms in the alkyl moiety, which is optionally monosubstituted or disubstituted in the phenyl moiety by identical or different substituents, suitable phenyl substituents being:

halogen, cyano, nitro, alkyl, alkoxy or alkylthio each having 1 or 2 carbon atoms, halogenoalkyl, halogenoalkoxy or halogenoalkylthio each having 1 or 2 carbon atoms and 1 to 5 identical or different halogen atoms—in particular fluorine, chlorine and/or bromine, alkoxycarbonyl or alkoximinoalkyl having 1 to 3 carbon atoms and phenyl which is optionally monosubstituted or disubstituted by identical or different fluorine, chlorine, bromine, methyl and/or ethyl substituents;

and additionally represents a radical

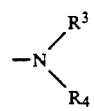

Het represents a heterocycle of the formula

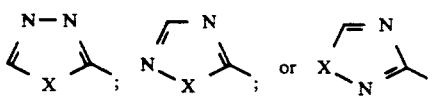

which is optionally monosubstituted or disubstituted by identical or different substituents, suitable substituents in each case being:

halogen, hydroxyl, mercapto, amino, cyano, nitro or carbamoyl, or alkyl, alkoxy, alkylthio, alkylsulphinyl, alkylsulphonyl, alkylamino, dialkylamino, alkanoylamino, halogenoalkylcarbonylamino or alkylaminocarbonylamino each having 1 to 4 carbon atoms in the individual alkyl moieties and optionally 1 to 7 identical or different halogen atoms—in particular fluorine, chlorine and/or bromine, and each of which is straight-chain or branched, alkenyl or alkinyl each having 2 to 4 carbon atoms and each of which is straight-chain or branched, straight-chain or branched alkylideneamino having 1 to 3 carbon atoms, halogenoalkyl, halogenoalkoxy, halogenoalkylthio, halogenoalkylsulphinyl or halogenoalkylsulphonyl each having 1 to 3 carbon atoms and 1 to 7 identical or different halogen atoms and each of which is straight-chain or branched, straight-chain or branched alkoxycarbonyl having 1 to 4 carbon atoms, cycloalkyl having 3 to 6 carbon atoms and phenyl, benzyl, phenylethyl, benzylideneamino or benzylaminocarbonylamino, each of which is optionally monosubstituted or disubstituted in the phenyl moiety by identical or different fluorine, chlorine, bromine, methyl, ethyl, methoxy, ethoxy and/or trifluoromethyl substituents and X represents oxygen, sulphur, an NH group an N-methyl group or an N-ethyl group, where R³ represents hydrogen or straight-chain or branched alkyl having 1 to 3 carbon atoms, which is optionally monosubstituted, suitable alkyl substituents being:

cyano, alkoxy, alkylthio, alkylamino or dialkylamino each having 1 or 2 carbon atoms in the individual alkyl moieties and phenyl which is optionally monosubstituted or disubstituted by identical or different fluorine, chlorine, bromine, methyl and/or ethyl substituents;

additionally represents straight-chain or branched halogenoalkyl having 1 to 3 carbon atoms and 1 to 7 identical or different halogen atoms—in particular fluorine, chlorine and/or bromine, additionally represents alkenyl or alkinyl each having 2 to 4 carbon atoms and each of which is straight-chain or branched, straight-chain or branched alkoxy having 1 to 3 carbon atoms or cycloalkyl having 3 to 6 carbon atoms and R⁴ represents straight-chain or branched alkyl having 1 to 3 carbon atoms, which is optionally monosubstituted, suitable alkyl substituents being:

cyano, alkoxy, alkylthio, alkylamino or dialkylamino each having 1 or 2 carbon atoms in the individual alkyl moieties and phenyl which is optionally monosubstituted or disubstituted by identical or different fluorine, chlorine, bromine, methyl and/or ethyl substituents;

additionally represents straight-chain or branched halogenoalkyl having 1 to 3 carbon atoms and 1 to 7 identical or different halogen atoms—in particular fluorine, chlorine and/or bromine, additionally represents alkenyl or alkinyl each having 2 to 4 carbon atoms and each of which is straight-chain or branched, straight-chain or branched alkoxy having 1 to 3 carbon atoms or cycloalkyl having 3 to 6 carbon atoms or R³ and R⁴, together with the nitrogen atom to which they are bonded, represent a 1-pyrrolidinyl, 1-piperidinyl, 1-perhydroazepinyl or 4-morpholinyl radical which is optionally monosubstituted or disubstituted by identical or different methyl and/or ethyl and/or methoxy substituents.

5. A compound according to claim 1 wherein such compound is of the formula

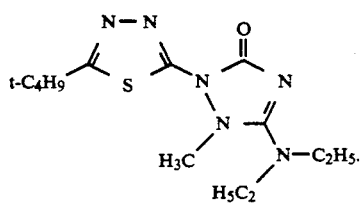

6. A compound according to claim 1 wherein such compound is of the formula

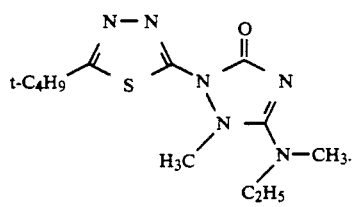

7. A compound according to claim 1 wherein such compound is of the formula

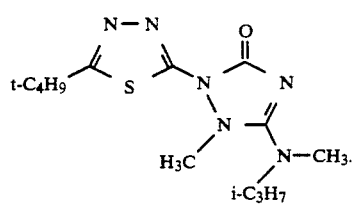

8. A compound according to claim 1 wherein such compound is of the formula

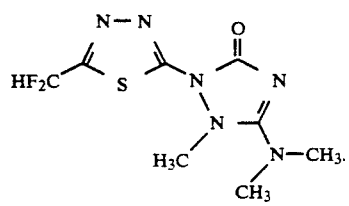

9. A compound according to claim 1 wherein such compound is of the formula

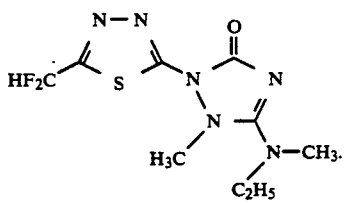

10. A compound according to claim 1 wherein such compound is of the formula

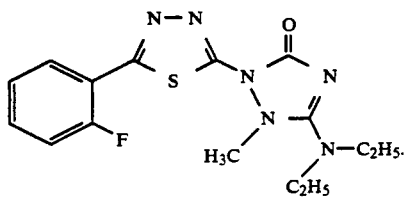

11. A compound according to claim 1 wherein such compound is of the formula

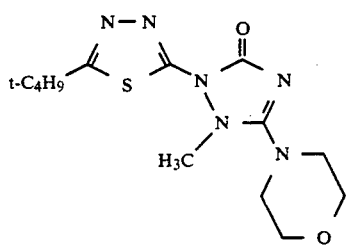

12. A compound according to claim 1 wherein such compound is of the formula

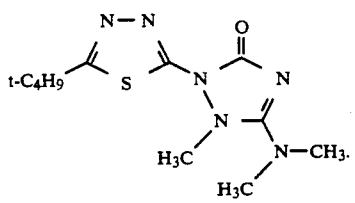

13. A herbicidal composition comprising a herbicidally effective amount of a compound according to claim 1 and a diluent.

14. A method of combating unwanted vegetation which comprises applying to such vegetation or to a locus from which it is desired to exclude such vegetation a herbicidally effective amount of a compound according to claim 1.

15. The method according to claim 14, wherein such compound is of the formula

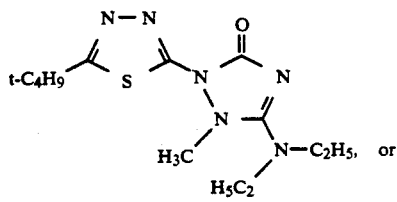

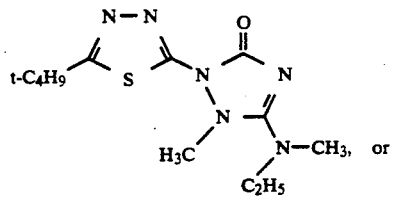

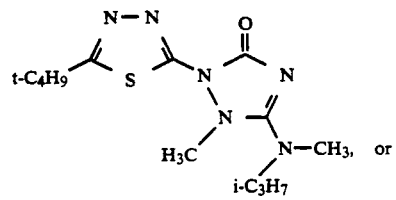

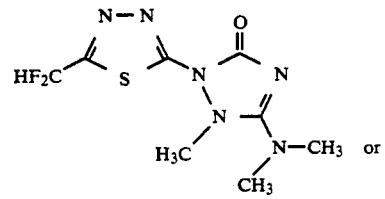

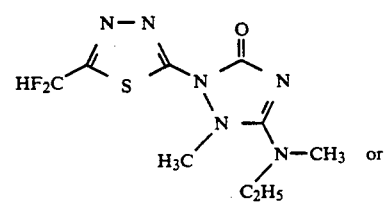

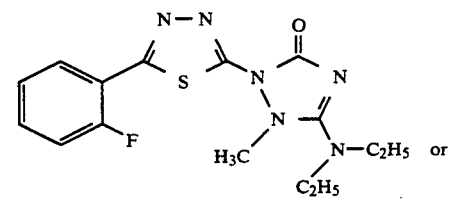

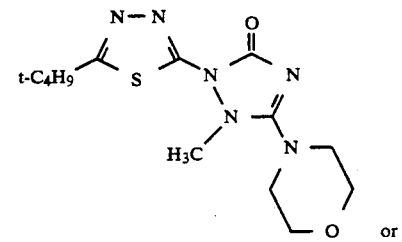

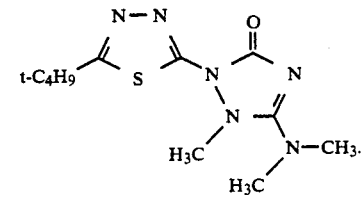

* * * * *